US008247545B1

(12) United States Patent
Colpan

(10) Patent No.: US 8,247,545 B1
(45) Date of Patent: Aug. 21, 2012

(54) DEVICE AND A PROCESS FOR THE ISOLATION OF NUCLEIC ACIDS

(75) Inventor: Metin Colpan, Essen (DE)

(73) Assignee: Qiagen GmbH, Hilden (DE)

( * ) Notice: Subject to any disclaimer, the term of this patent is extended or adjusted under 35 U.S.C. 154(b) by 1826 days.

(21) Appl. No.: 08/796,040

(22) Filed: Feb. 5, 1997

Related U.S. Application Data

(63) Continuation of application No. 08/244,530, filed on Aug. 2, 1994, now abandoned.

(30) Foreign Application Priority Data

Dec. 2, 1991 (DE) .................................. 41 39 664

(51) Int. Cl.
*C07H 21/00* (2006.01)
(52) U.S. Cl. ..................................... 536/25.4
(58) Field of Classification Search ................ 536/25.4; 422/70; 436/6; 435/6
See application file for complete search history.

(56) References Cited

U.S. PATENT DOCUMENTS

| | | | | |
|---|---|---|---|---|
| 3,433,782 | A * | 3/1969 | Kreiser | 536/25.4 |
| 3,821,193 | A * | 6/1974 | Fare et al. | 536/23.1 |
| 3,935,111 | A | 1/1976 | Bentley | |
| 4,087,363 | A | 5/1978 | Rosemeyer et al. | |
| 4,303,530 | A | 12/1981 | Shah et al. | |
| 4,623,723 | A * | 11/1986 | Keller et al. | 536/25.4 |
| 4,643,981 | A | 2/1987 | Card | |
| 4,699,717 | A * | 10/1987 | Riesner et al. | 536/25.4 |
| 4,810,381 | A | 3/1989 | Hagen et al. | 210/502.1 |
| 4,921,952 | A * | 5/1990 | Longmire et al. | 536/25.41 |
| 4,923,978 | A * | 5/1990 | McCormick | 536/25.4 |
| 4,925,572 | A * | 5/1990 | Pall | 210/767 |
| 4,935,142 | A | 6/1990 | Sterberg | 210/634 |
| 4,935,342 | A * | 6/1990 | Seligson et al. | 435/6 |
| 4,997,932 | A * | 3/1991 | Reardon et al. | 536/25.4 |
| 5,057,426 | A * | 10/1991 | Henco et al. | 435/270 |
| 5,075,430 | A | 12/1991 | Little | 536/25.4 |
| 5,342,931 | A * | 8/1994 | Woodard et al. | 536/25.4 |
| 6,020,186 | A * | 2/2000 | Henco et al. | 435/287.2 |

FOREIGN PATENT DOCUMENTS

| | | |
|---|---|---|
| CH | 674713 A5 | 7/1990 |
| DE | 1 260 470 | 2/1968 |
| DE | 30 20 449 | 12/1980 |
| DE | 33 08 932 A1 | 9/1984 |
| DE | 36 39 949 A1 | 6/1988 |
| DE | 37 17 209 A1 | 12/1988 |
| DE | 37 17211 A1 | 12/1988 |
| DE | 39 13814 A1 | 7/1990 |
| DE | 40 34 036 A1 | 4/1992 |
| EP | 0268946 * | 6/1988 |
| EP | 0268946 A * | 6/1988 |
| EP | 0270017 * | 6/1988 |
| EP | 0270017 A * | 6/1988 |
| EP | 0 288 425 | 10/1988 |
| EP | 0 364 173 | 4/1990 |
| EP | 0 376 080 | 7/1990 |
| EP | 0376080 | 7/1990 |
| EP | 389063 | 9/1990 |
| EP | 0 406 485 A1 | 1/1991 |
| JP | 53-012900 A * | 2/1978 |
| JP | 0012900 * | 2/1978 |
| SU | 638599 * | 12/1978 |
| SU | 0638599 * | 12/1978 |
| WO | WO 87/07654 | 12/1987 |
| WO | 9105606 | 3/1991 |
| WO | 9107422 | 5/1991 |
| WO | WO 92/00132 | 1/1992 |
| WO | 92/07863 | 5/1992 |
| WO | 9311221 | 6/1993 |

OTHER PUBLICATIONS

*International Dictionary of Medicine and Biology*, vol. 1, John Wiley & Sons, New York, NY, 1986, only title pages and p. 522 supplied.*
Hames et al., Nucleic Acid Hybridisation—A Practical Approach, IRL Press, Washington, DC, 1985, only title pages and text/index pp. 64-65 and 235 supplied.*
Anon., International Dictionary of Medicine and Biology, vol. 1, John Wiley & Sons, New York, NY, 1986, only title pages and p. 522 supplied.*
M.A. Marko et al., "Procedure for the Large-Scale Isolation of Highly Purified Plasmid DNA Using Alkaline Extraction and Binding to Glass Powder", XP000602405, pp. 382-387, Apr. 1982.
Takahatu Mizutani, "Adsorption Chromatography of Nucleic Acids on Silicone-Coated Porous Glass", *J. Biochem*. vol. 94, (1983), pp. 163-169. (Jul. 1983).
ISBN 4-06=129832-1 (1) (KS), NDC 579, 325 p. 22 cm., B. Hagiwara and K. Hashimoto (1974) (with partial English language translation).
Brockhaus, Mannheim, *Naturwissenschaften und Technik*, Sonderausg, 1989, 117. "Naturwissenschaften und Technik" = "Science and Technology".

* cited by examiner

*Primary Examiner* — Lawrence E Crane
(74) *Attorney, Agent, or Firm* — Jacobson Holman PLLC

(57) ABSTRACT

There is described is a process for the isolation and purification of nucleic acids such as plasmid or genomic DNA from cells or other sources, wherein
a) the cells containing nucleic acids are digested and cell debris is removed, or other samples containing nucleic acids are treated with anion exchangers, namely, in buffer solutions of low ionic strength,
b) thereafter, the nucleic acids are desorbed from the anion exchanger using a buffer of high ionic strength, in order to be subsequently
c) treated in said buffer of high ionic strength or in the presence of lower alcohols and/or poly(ethylene glycol) with a mineral support material, with adsorption of the nucleic acid to the surface of the mineral support materials, whereupon
d) desorption of the nucleic acid is effected using water or a buffer solution of low ionic strength.

Figure 1:
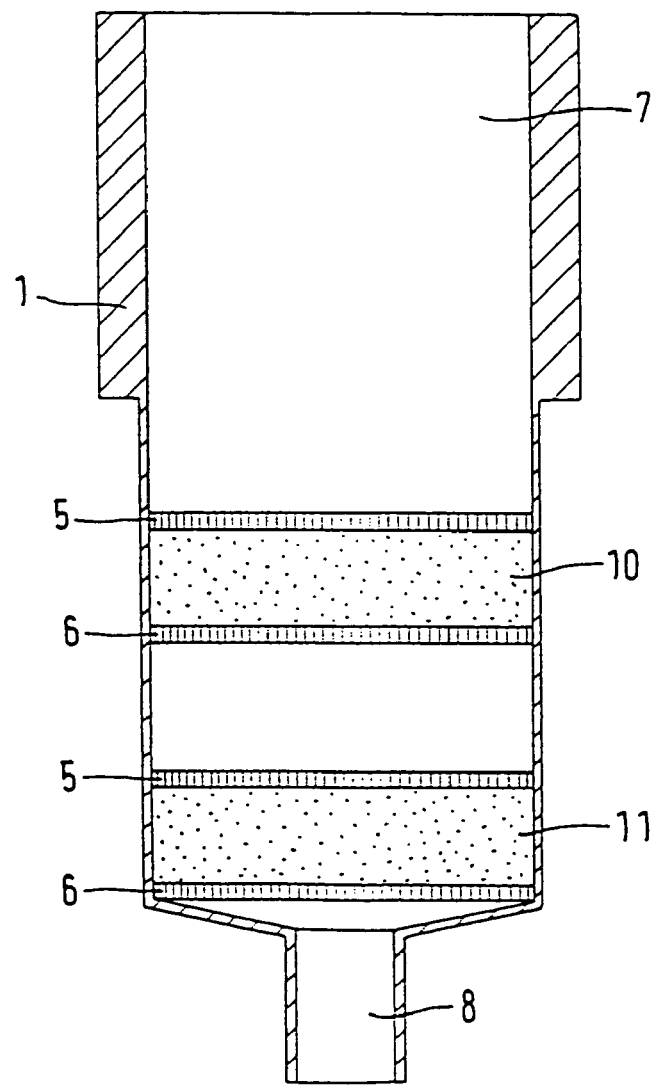

The device for operating the inventive process consists of a hollow body (1) with an inlet opening (7) and an outlet opening (8), wherein in the hollow body (1), between two securing means (5, 6), a powdered first material based on silica gel (10) is arranged, and a second material (11) is placed between the first material (10) and the outlet opening (8), the first and second materials (10, 11) having different adsorption characteristics for nucleic acids.

19 Claims, 10 Drawing Sheets

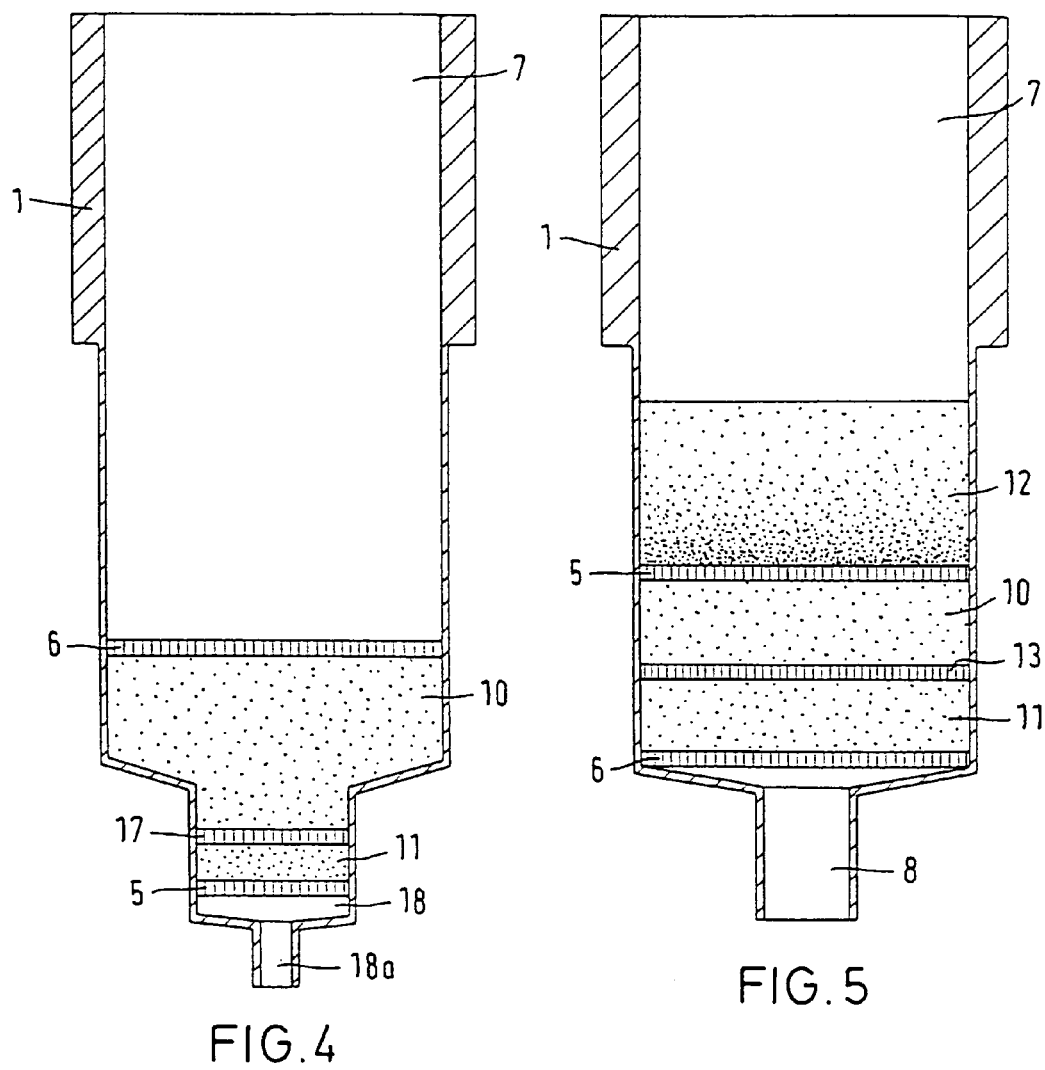

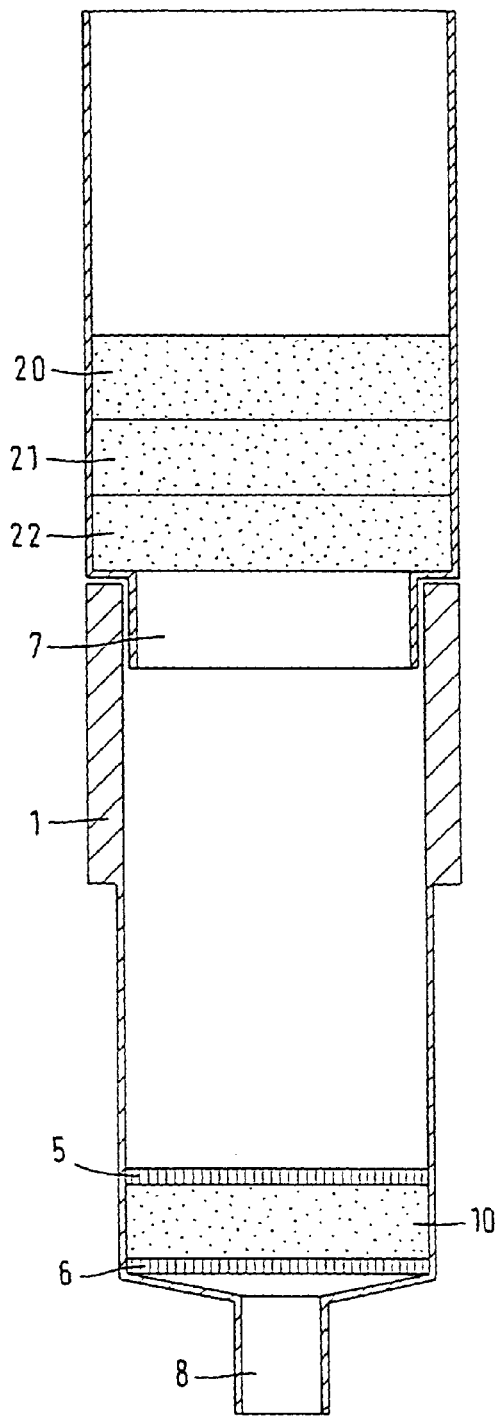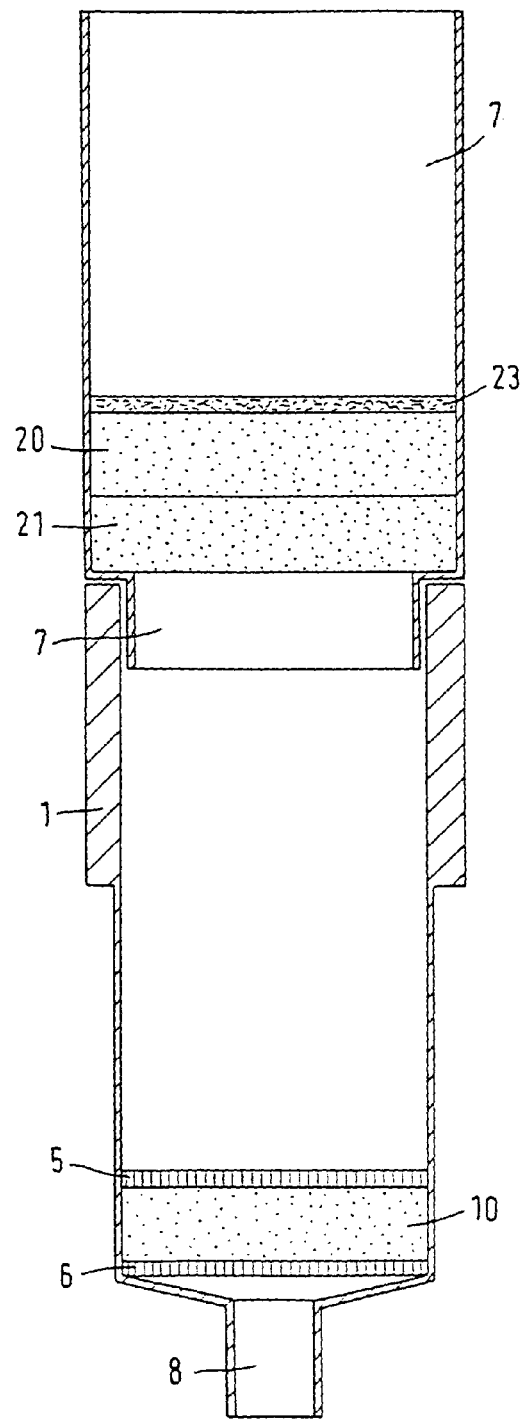

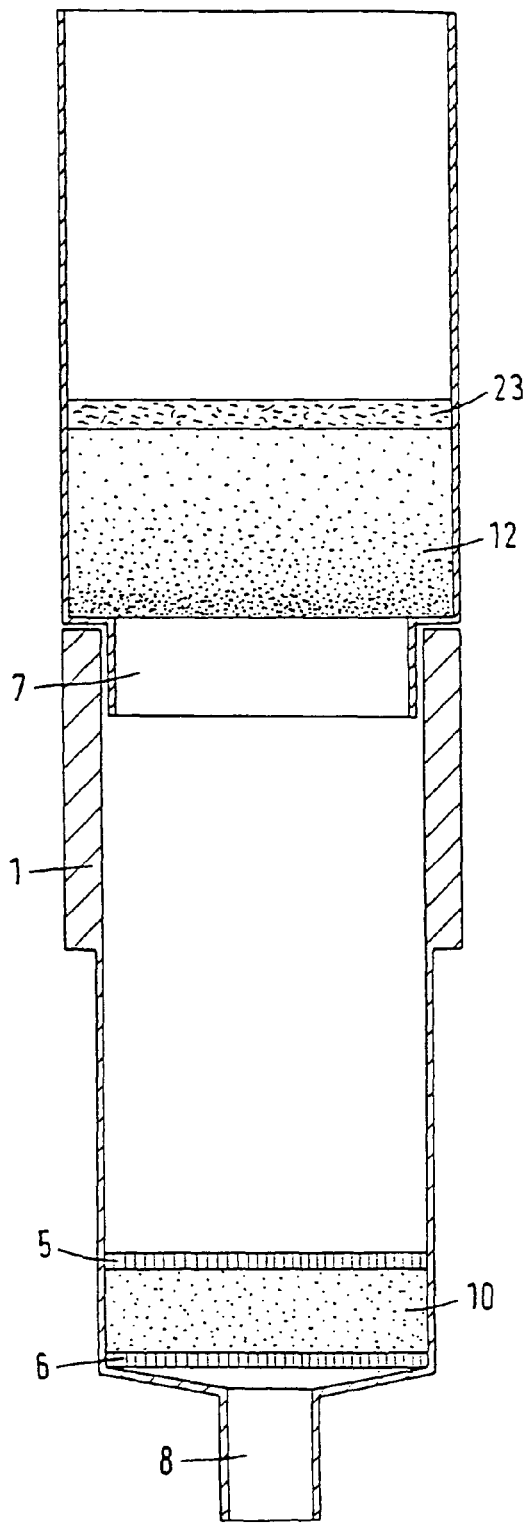
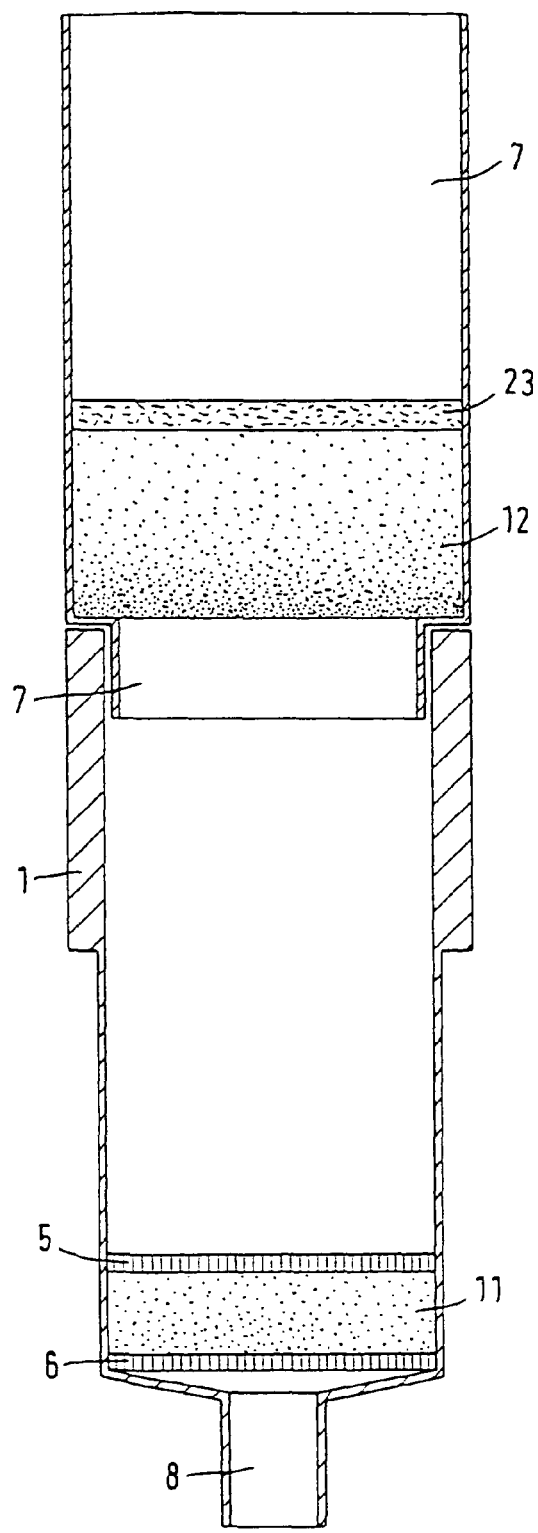

DEVICE AND A PROCESS FOR THE ISOLATION OF NUCLEIC ACIDS

This application is a continuation of application Ser. No. 08/244,530, filed on Aug. 2, 1994 now abandoned.

This invention is directed to a process for the isolation and purification of nucleic acids such as plasmid or genomic DNA from cells or other sources and to a device for operating the process according to the preamble of Claim 16.

In the preparation of nucleic acids, the cells have to be digested first by using enzymes such as, for instance, proteinase K and lysozyme, detergents such as SDS, Brij, Triton-X-100, Tween 20, and DOC, and chemicals such as sodium hydroxide, guanidine hydrochloride and guanidine isothiocyanate. The experimenter is confronted with the problem to remove cell debris prior to purification of the nucleic acids and then to isolate the nucleic acids or nucleic acid fractions from the cell lysate. Furthermore, when preparing plasmid DNA or genomic DNA, detergents frequently used such as SDS (sodium dodecylsulfate) must be removed. In most of the cases when using SDS, this is effected by precipitation with potassium acetate since the SDS potassium salt is sparingly soluble. Then, the cell debris is centrifuged together with the precipitated SDS. As the components in the lysate produce an exceedingly voluminous and sludgy, gel-like pellet, removal of said debris is difficult even in a high-speed centrifuge. Conventionally, cell debris removal is effected by centrifugation between from 5,000 g to 20,000 g for 15 to 60 minutes. This procedure suffers from the drawback that it requires a very high input of time and work and cannot be automatized.

The DE-A-36 39 949 describes a process for the isolation and purification of long-chain nucleic acids from other substances from bacteria, viruses, animal and plant tissue and cells, as well as body fluids, in particular, cell ingredients and/or their degradation products, as well as components of body fluids which are not long-chain nucleic acids. Here, the long-chain nucleic acids, subsequent to mild digestion and removal of cell debris and other undissolved components are fixated to an anion exchanger while the substances to be separated are washed off. Thereafter, the fixated nucleic acids are removed from the matrix by using a buffer of high ionic strength.

From DE-A 37 17 211, there is known a process for the separation and purification of biopolymers such as nucleic acids, wherein the nucleic acids are adsorbed in a matrix arranged in a special device. Here, the buffer conditions are adjusted such that the nucleic acids are adsorbed predominantly, while interfering substances such as proteins, low molecular weight substances or cell debris as well are not bound.

In "Isolierung, Fraktionierung und Hybridisierung von Nukleinsäure, eine Einführung und methodische Anleitung", edited by Ulrich Wobis, Verlag Chemie, 1980, there are described methods for the isolation of nucleic acids. Therefrom, it follows that high molecular weight ribonucleic acids are insoluble in salt solutions of >1.5 M sodium chloride and undergo precipitation. However, such precipitation is not regarded as efficient, so that in this monograph, multiple repetitions of the precipitation steps using high salt concentrations are recommended.

Efficient separation of both DNA restriction fragments and amplified products of the polymerase chain reaction is described in J. Chromatogr., 1990, 512, 433-444. As the chromatographic material, an ionic exchanger DEAD NPR material having non-porous particles 2.5 μm in size is used.

Nucleic acids from yeasts have been separated according to Biochemistry 1972, 4848 on poly-L-lysine-coated kieselguhr. Likewise, mitochondrial DNA has been separated on such chromatographic materials.

In Chromatographia, 1984, 19, 236-9, the use of multidimensional chromatography for isolating synthetic oligodeoxyribonucleotides on a preparative scale is described. Here, in a first step, a size exclusion chromatography on Sephadex G-15 is conducted, followed by size exclusion chromatography using an HPLC ion exchanger column (Partisil-10 SAX). This is followed by hydrophobic chromatography using HPLC (Nucleosil C18).

J. Biochem. 94, 163-169 (1983) reports on suitability of hydrophobic-coated glass particles for conducting adsorption-chromatographic purification of nucleic acids.

A disadvantage in this substitute prior art is the fact that a centrifugation step for removing cell fragments and undissolved components from the cell lysate is necessary. Another problem is that due to elution in buffers of high ionic strength, the nucleic acids must be recovered from salts present in high concentration and at the same time, must be concentrated. By far in most of the cases, further process operations with the thus obtained nucleic acids is possible only at buffer conditions of lower ionic strength. Removal of salts dissolved in the buffer at high concentration may also be effected by dialysis, but this gives rise to significant degradation of the nucleic acids in the corresponding samples. Following dialysis, the desalted nucleic acid must be concentrated by freeze-drying. Another way of concentration is effected by precipitating the nucleic acid with ethanol, isopropanol, polyethylene glycol) (PEG). The nucleic acids are insoluble in this system and are precipitated. However, the precipitated nucleic acids must be pelletized by a centrifugation step. The nucleic acid pellet is briefly dried and subsequently, dissolved in a low volume buffer of exceedingly low salt concentration to obtain a concentrated salt-free nucleic acid sample. By using such centrifugation and precipitation processes, simple and quick recovering of nucleic acids is not possible, and automatization is only difficult to achieve. On the other hand, there is an increasing demand in simple and automatic processes for preparing nucleic acids due to the advancement of molecular biology in clinical diagnostics and the human genome sequencing where in each case, large amounts of samples must be processed.

The technical problem which the invention is based upon is to provide a process enabling to isolate and purify nucleic acids without the requirement of a centrifugation step to remove cell fragments or undissolved components of the cell lysate and without obtaining the nucleic acids in buffer systems having high salt concentrations where the nucleic acids require a subsequent desalting and concentrating step. Virtually, the process to be provided is to deliver the nucleic acids in a condition permitting direct further processing. Another important aspect of the technical problem mentioned is to create a device enabling to operate the process in a particularly advantageous fashion.

The technical problem which the invention is based upon is solved in a surprisingly simple manner by a process characterized by the features, and preferred embodiments of the process according to the invention.

A device enabling to operate the process of the invention in a particularly advantageous fashion is characterized by the features, and preferred embodiments of the device according to the invention.

Initially, the cells from which the nucleic acid is to be isolated are digested in the usual manner, and cell debris is removed. This may be accomplished by filtration or centrifugation. Preferably, recovery is effected by filtration on a filter layer which is made up in steps or asymmetrically. The filtrate containing the nucleic acids may be treated with anion exchangers immediately. As the anion exchanger, a commercially available material may be selected which permits bonding of the nucleic acid to be isolated, under the respective conditions of preparation. Preferably, the anion exchangers are surface-modified supports made of a matrix, preferably consisting of agarose, dextran, cellulose, acrylic amide, poly(vinyl alcohol), polystyrene, glass, aluminum oxide, titanium dioxide, zirconium dioxide, or silica gel, such as, e.g., DEAE Sepharose®, Q Sepharose®, DEAE Sephadex®, DEAE Toyopearl®, Amberlite®, Nukleogen®, Qiagen®. The anion exchangers may be porous support materials having a high capacity internal surface suitable for interaction, or may be non-porous support materials which undergo interaction with the mixture to be separated on the outer surface only. It is particularly preferred when the anion exchanger is a material on the basis of silica gel, which has a particle size of from 1 to 250 µm, preferably from 10 to 50 µm, and particularly preferred from 15 to 25 µm, and a pore diameter of from 1 to 2,500 nm, preferably from 10 to 500 nm, particularly preferred from 100 to 400 nm. In particular, proven to be an anion exchanger material has a material having high surface charge and high binding capacity for nucleic acids. Preferably, silica gel modification is effected by silanizing the support material as is disclosed, for instance, in EP-A 83 901 065, DE-A-39 35 098 and U.S. Pat. No. 5,057,426. In the EP-A 83 901 065, for example, γ-glycidyloxypropyltrimethoxysilane and N,N-dimethylaminoethanol are used to modify the support material.

Adsorption of the nucleic acids is effected under conditions as are typically present at low salt concentrations. Preferably, these are lower salt concentrations than those enabling the nucleic acids to be eluted from the column. Here, depending on ion exchanger materials and pH values used, the salt concentration may be from 0.25 to 1.5 M.

Adsorption of the nucleic acids to the anion exchanger material may be followed by at least one washing step using a buffer of low ionic strength.

Here, preferably, the ion exchanger material is placed in a predominantly cylindrical hollow body of a column. Then, the column is washed with a salt solution having an ionic strength as high as possible, without the nucleic acids being eluted. Thereby, low molecular weight and weakly charged impurities and proteins are washed off.

In order to avoid unnecessary losses in yield, it may be advantageous to effect conditioning of the respective adsorptive materials between the adsorption step and the elution step or as the last washing step by realizing an ionic strength as high as possible, particularly in that area where subsequently, adsorption of the nucleic acid under high salt conditions is to be effected. In particular, to this end, a solution for equilibrating and conditioning may be used, corresponding to an ionic strength of about 1.5 M sodium perchlorate at a pH of approximately 5.

Correspondingly, the material for binding the nucleic acids under conditions of high ionic strength is placed in a separate, predominantly cylindrical hollow body. The nucleic acid fraction desorbed from the ion exchanger material and being in the high salt fraction is placed into the cartridge or the column containing the material adsorbing nucleic acids under high salt conditions. In a preferred embodiment, each device is adjusted to the corresponding adsorptive materials in such way that the container with anion exchanger may be arranged on top of the container with material adsorbing nucleic acids under high salt conditions.

In particular, conditioning of the material capable of adsorbing the nucleic acids at high ionic strength is easily possible with such a way of proceeding. Conditioning may already be effected by pretreating the material capable of binding the nucleic acids at high ionic strength with correspondingly highly concentrated salt solutions. However, it is also possible to use appropriately pretreated material, for example, by initially treating the material adsorbing nucleic acids with salt solutions of high ionic strength, so that very high salt concentrations result in the material adsorbing nucleic acids under high ionic strength immediately when an aqueous solution is contacted therewith. Conditioning is advantageous due to the fact that the first volumes separating from the material by elution of the nucleic acids from the anion exchanger possibly have a salt concentration still too low to adsorb sufficiently strong to the following material. Now, if a relatively dilute elution droplet gets in contact with thus conditioned material capable of bonding the nucleic acids under conditions of high ionic strength, a high salt concentration results immediately, and the nucleic acids will be adsorbed to this material.

Thereafter, the nucleic acid may be desorbed from the anion exchanger material using a buffer of high ionic strength in order to be bonded to a mineral support immediately in the elution buffer of high ionic strength. In the presence of chaotropic salts such as sodium iodide and sodium perchlorate, nucleic acids may be bound to finely ground glass or silica gel, if the fine glass or silica gel suspension is added to the nucleic acids and incubation is effected for a prolonged period of time, in order to enable bonding of the nucleic acid to the silica gel (B. Vogelstein and D. Gillespie, 1979, Proc. Nat. Acad. Sci., U.S.A., 76, 615-19; Preparative and Analytical Purification of DNA from Agarose; R. Yang, J. Lis and B. Wu, 1979, Elution of DNA from Agarose after Gel Electrophoresis, Methods Enzymol. 65, 176-182; M. A. Marko, R. Chipperfield and H. C. Birnboim, 1982, A Procedure for the Large Scale Isolation of Highly Purified Plasmid DNA Using Alkaline Extraction and Binding to Glass Powder, Anal. Biochem. 121, 382-387).

Surprisingly, adsorption of the nucleic acids to mineral supports may also be effected by adding lower alcohols to the sample. Preferably, methanol, ethanol, propanol, isopropanol, and butanol are possible. The preferred ranges of quantity, in which the alcohols are added to the sample, are 1-50% (v/v) as far as they are soluble in water within these ranges at all. Furthermore, adsorption of the nucleic acids may be achieved by using poly(ethylene glycols). Usable ethylene glycols have molecular weights of from 1,000 to 100,000, particularly from 6,000 to 8,000. Addition of poly(ethylene glycol) may range from 1-30% of sample.

Surprisingly, the process according to the invention shows that nucleic acids are also efficiently adsorbed when passing very thin layers of glass or silica gel, although the residence time is only 1-30 s. Similarly, it is found that binding occurs in high concentrations of sodium chloride and lithium chloride and that chaotropic salts are not necessary. In addition, a combination of anion exchanger and silica gel has not been described so far, wherein the anion exchanger serves to purify the nucleic acid, and while at concentrations of from 0.25 to 1.5 M of salt, impurities such as metabolites, proteins and in part, RNA, and polysaccharides are removed, these are not capable of adsorbing to the downstream silica gel layer under the conditions given, and the silica gel layer serves the object of desalting and concentrating, when the nucleic acid in the following step is eluted from the anion exchanger at a salt concentration sufficiently high to enable nucleic acid adsorption to the silica gel layer.

For the step of adsorption to the mineral support, the following buffer salts in the concentrations indicated are possible:

| Salt | Concentration |
|---|---|
| NaCl | 3-5 M |
| NaClO$_4$ | 5-7 M |
| Gu-HCl | 5-7 M |
| NaI | 3-5 M |

The treatment with salt solution may be effected simply by dropping onto the filter and suction. In a preferred embodiment, the silica gel layer is treated with a perchlorate solution, pH from 6.5 to 8.5, in particular, from pH 7 to 8. Conveniently, this is done by pipetting and suction. Particularly preferred to this end is the use of a solution containing from 4 to 8 M of NaClO$_4$, from 5 to 20 mM of Tris-HCl, pH from 7 to 8, and from 0.5 to 2 mM of EDTA. Following removal of the chaotropic solutions, particularly the sodium perchlorate solution, rewashing is effected preferably using ethanol, for example, with 50-90% ethanol.

Once the filters are dried, elution is conducted in conventional fashion using a dilute aqueous salt solution such as, e.g., described in Anal. Biochem. 101, 339-341 (1980). A preferred eluant is 0.5-2 mM Tris-HCl, pH from 7 to 8, containing from 0.05 to 0.2 mM of EDTA, in the following referred to as TE. Further suitable eluants are dilute solutions of detergents such as, e.g., 0.1% of SDS which, however, are less preferred.

It was found that apart from silica gel, also other mineral supports are suitable for the adsorption of the nucleic acid. However, in a preferred embodiment, silica gel having a particle size of from 1 to 250 μm, preferably from 1 to 50 μm, and more specifically, from 1 to 5 μm, is used. The desalting layer may be employed in the extraction column as a loosely packed layer sandwiched by two PE frits. Another embodiment involves application of the mineral supports in the form of a membrane according to EP-0 323 055 (Dec. 7, 1988, 3M, Composition Chromatographic Article).

Using the process according to the invention, nucleic acids of most various provenance may be separated and prepared, irrespective whether the nucleic acids are derived from bacteria, cell cultures, blood, tissue, urine, viruses, or from amplification reactions such as PCR (polymerase chain reaction), SSSR (self-sustained sequence replication), ligase chain reaction, and similar reactions, or whether labeled nucleic acids, like those labeled in biotin, fluorescence-labeled or radioactively labeled nucleic acids are concerned. Possible as the nucleic acid are nucleic acids within a size range of from 10 nucleotides to 200,000 nucleotides. Nucleic acids in the meaning of the invention are understood to be oligonucleotides having from 10 to 100 nucleotides, RNA having from 50 to 25,000 nucleotides, plasmid DNA having from 2,500 to 25,000 base pairs, cosmid DNA having from 5,000 to 60,000 base pairs, or genomic DNA having from 100 to 200,000 base pairs.

The nucleic acid fraction(s) obtained according to step d) of the process according to the invention are obtained in solutions having low salt load. Thus, subsequent adjustment of buffer conditions required for further processing is possible. In a particularly convenient fashion, the nucleic acid bound to the silica glass is already eluted in the buffer designed for further processing.

The isolated nucleic acids are employed for most various applications. Particularly frequently, enzymatic reaction is effected using restriction enzymes, polymerases and ligases for restriction analysis, sequencing, labeling with radioactivity or non-radioactive markers such as biotin, FITC, digoxigenin, and amplification using PCR, SSSR, and ligase chain reaction.

The process of the invention is particularly suitable for the isolation and preparation of plasmid DNA and genomic DNA.

The Figures illustrate preferred embodiments of the device according to the invention, wherein the various adsorptive materials for the nucleic acids are combined in one device.

FIG. 1 shows a device for operating the process according to the invention, consisting of a hollow body 1 having an inlet opening 7 and an outlet opening 8. Preferably, the hollow body consists of polypropylene (PP), polyethylene (PE), poly (methyl methacrylate) (PMMA), polytetrafluoroethylene (PTFE), poly(ethyl terephthalate) (PET), or polyacrylonitrile (PAN). In the hollow body 1, between two securing means 5 and 6, a powdered first material of a mineral support material 10 is arranged. In the hollow body 1, a second powdered material 11 of a mineral support material is placed between the first material 10 and the outlet opening 8. First and second materials 10, 11 have different adsorption characteristics for nucleic acids. The differences in adsorption characteristics are determined by different adsorption behavior in buffers of high and low ionic strength, respectively. For instance, where nucleic acids are bound by the first material 10 under conditions of low ionic strength, then the second material 11 must be capable of permitting the nucleic acids to pass readily under buffer conditions of low ionic strength, whereas under conditions of high ionic strength, the nucleic acid will be desorbed from the first material 10 and adsorbed to the second material 11.

Preferably, the first powdered material 10 consists of an anion exchanger of surface-modified supports on the basis of agarose, dextrans, cellulose, acrylic amide, poly(vinyl alcohol), polystyrene, glass, aluminum oxide, titanium dioxide, zirconium dioxide, or silica gel, particularly, anion exchangers of the type mentioned above on the basis of silica gel. The preferably basic ion exchanger has a particle size of from 10 to 40 μm, particularly from 15 to 25 μm, more specifically from 15 to 25 μm, and a pore diameter of from 1 to 2,500 nm, preferably from 10 to 500 nm, particularly from 200 to 400 nm.

The second material 11 is a mineral support material, particularly of silica gel, glass, zeolite, aluminum oxide, titanium dioxide, zirconium dioxide, kaolin, diatomacae, preferably a silica glass, optionally in the form of a silica gel suspension. The second material 11 preferably has a particle size of from 1 to 250 μm, particularly from 1 to 30 μm, with 1 to 5 μm being preferred.

Preferably, the devices 5 and 6 consist of sintered glass (frits) or membranes of plastics such as polyethylene, PTFE, polypropylene, glass, ceramics, Nylon, or a non-woven made of polypropylene, polyethylene, Nylon. Preferably, the porosity of the devices 5, 6 is from 10 to 500 μm.

Figure 2:
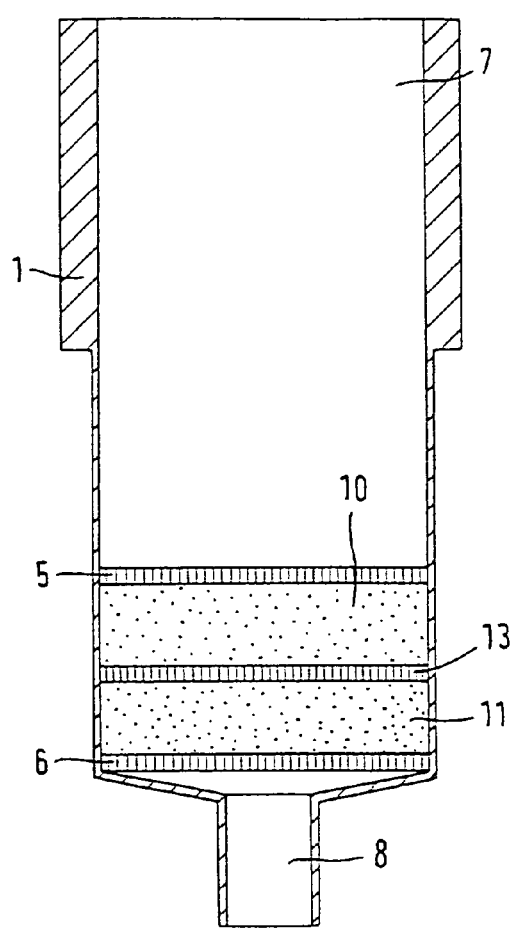

Another preferred embodiment of the device of the invention is illustrated in FIG. 2. Therein, the first material 10 and the second material 11 are arranged in the hollow body 1 in such way that the materials 10, 11 are directly adjacent and namely, in separate layers which together are held by the securing means 5 and 6. Preferably, the material may be separated by a separating means 13, said separating means 13 being a porous pane, preferably of sintered glass, or a plastic membrane or a tissue, preferably of Nylon.

Figure 3:
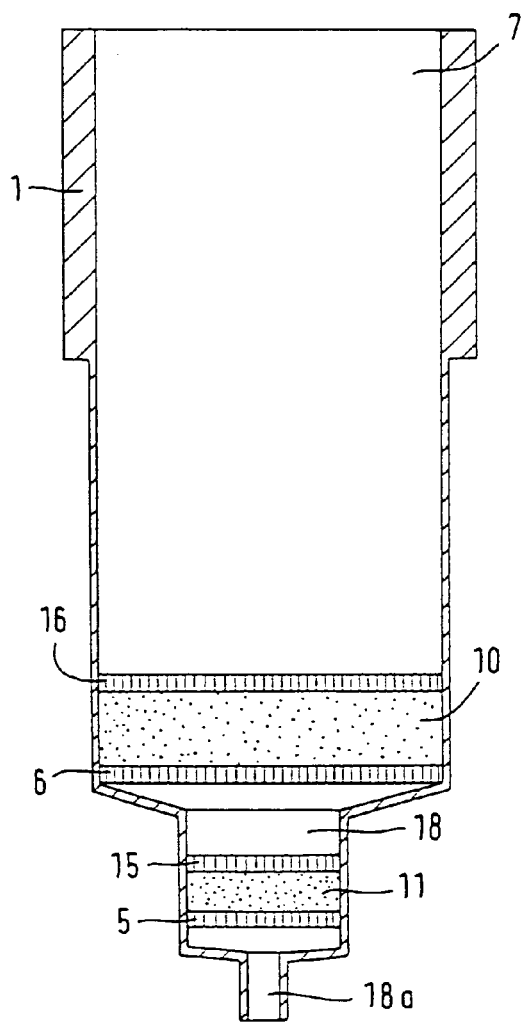

FIG. 3 illustrates another preferred embodiment of the device according to the invention, wherein the second material 11 is secured in the outlet 18 forming a channel, between the securing means 5, 15. The outlet opening 18 forming a channel has a smaller cross-section than the hollow body 1 and preferably ends in a channel 18a, the diameter of which being smaller than that of channel 18. The first material 10 is placed within the lumen of hollow body 1 in the area of the longer diameter and is secured by means 6, 16. Here, it may be advantageous to allow the first and second materials 10, 11 to be adjacent, so that they are separated only by a common means 17 (see FIG. 4).

FIG. 5 describes another preferred embodiment of the device of the invention which, in addition to the layers of first and second materials 10, 11, has another layer 12 within the hollow body, arranged on top of the first material 10. The layer 12 is designed as a mechanical filter means. Preferably, the third layer 12 is an asymmetrical filter, with the filter pore size decreasing in the sample flow direction, i.e., from feed opening 7 to outlet opening 8 or 18. Thereby, cell debris in the sample may be removed without the danger of jamming the device.

In all the embodiments of the device according to the invention, the materials 10 and 11 either may be in the form of a powder or designed as a molded body. Where the materials 10 and 11 are present in the form of particles, it may be recommendable to embed them into a supporting net of inert plastics, so that the layers are present in the form of a membrane according to U.S. Pat. No. 4,810,381 and U.S. Pat. No. 4,699,717 and as proposed in DE 41 27 276. The supporting net may consist of Teflon.

Figure 6:
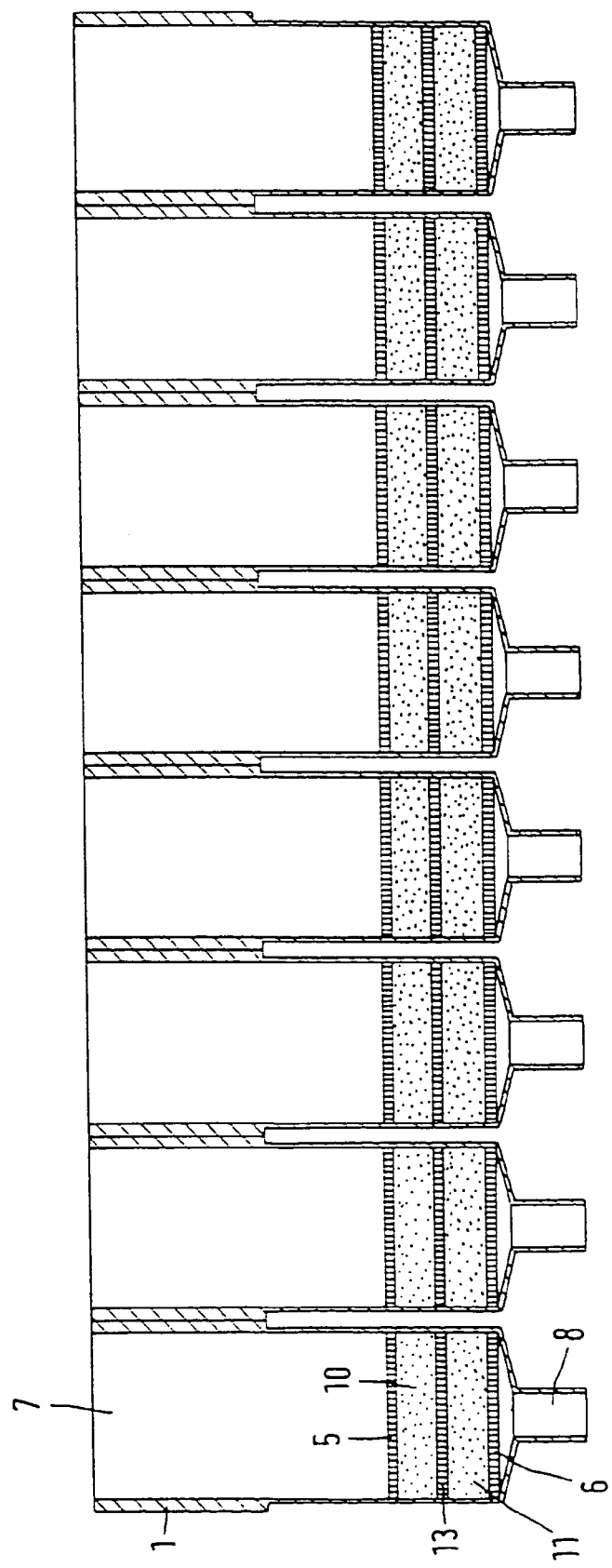

FIG. 6 describes a further preferred embodiment of the device according to the invention, wherein eight individual, separate devices according to FIG. 2 are adjacent to each other, forming a unit of eight. The advantage of this embodiment which may be realized with each of the individual embodiments described in 1-5, is based on the parallel preparation of 8 samples with the aid of multichannel pipettes. Similarly, this design may also be produced in a 12 times lined-up form, thereby making 96 samples processable. The great advantage is given in those cases where the internationally standardized microtiter format is used.

FIG. 7 describes a device containing in a cylindrical hollow body 1 with inlet opening 7 and outlet opening 8 an anion exchanger material 10 secured between two means 6 and 5. Attached thereon is another cylindrical hollow body, in the lumen of which various filter layers are arranged. The filter layers 20, 21, 22 may consist of sintered polyethylene, polypropylene, PTFE, glass, silica gel, aluminum oxide or packed diatomaceous earth, e.g., Cellit or silica gel. However, a woven, bonded fleece of polypropylene, polyester, glass fiber, and silica is likewise possible. Preferably, the porosity of the single layers is from 15 µm to 500 µm at a thickness of from 0.1 to 10 mm. The pore size of the filter layer, as viewed in flow direction, decreases from layer to layer. In a typical embodiment, the pore size in layer 20 is about from 100 to 300 µm, in layer 21 from 30 to 100 µm, and in the third filter layer from 5 to 30 µm.

FIG. 8 illustrates a further preferred embodiment of the device according to FIG. 7, wherein as the top filter layer 23—as viewed in flow direction—a hydrophobic layer is inserted. The hydrophobic interlayer prevents undesirable penetration of the crude cell lysate into the filter layer prior to the onset of the actual filtration. Preferably, the hydrophobic interlayer 23 consists of spun or sintered polypropylene, polyethylene, polyester or polytetrafluoroethylene (PTFE) fibers, with a porosity of from 10 to 500 µm and preferably, a thickness of from 0.1 to 5 mm.

FIG. 9 describes a filtration device similar in design as those described in FIGS. 7 and 8, with the difference that different filter layers having decreasing pore size are combined in a single filter layer 12 of continuously decreasing pore size. Preferably, the asymmetric filter layer 12 is provided with a hydrophobic filter layer 23 at the top end, viewed in flow direction. Preferably, the asymmetric filter layer 12 consists of spun polypropylene or polyester fibers. Commercially available are profiles, for example by Pall Filtertechnik, Dreieich, Frankfurt, having porosity gradations of from 500 to 50 µm, from 100 to 10 µm, from 50 to 5 µm, and from 10 to 0.1 µm. Preferably, the thickness of the asymmetric filter layer should be from 1 to 10 mm.

FIG. 10 describes filtration devices for the separation of nucleic acids in the meaning of the invention, where again, the filter configuration of FIG. 9 is used and wherein the asymmetric filter layer is provided with a hydrophobic filter layer 23. Instead of the anion exchanger 10, there is placed into the hollow body 1a mineral support 11 capable of adsorbing nucleic acids in highly concentrated salt solutions.

Figure 11:
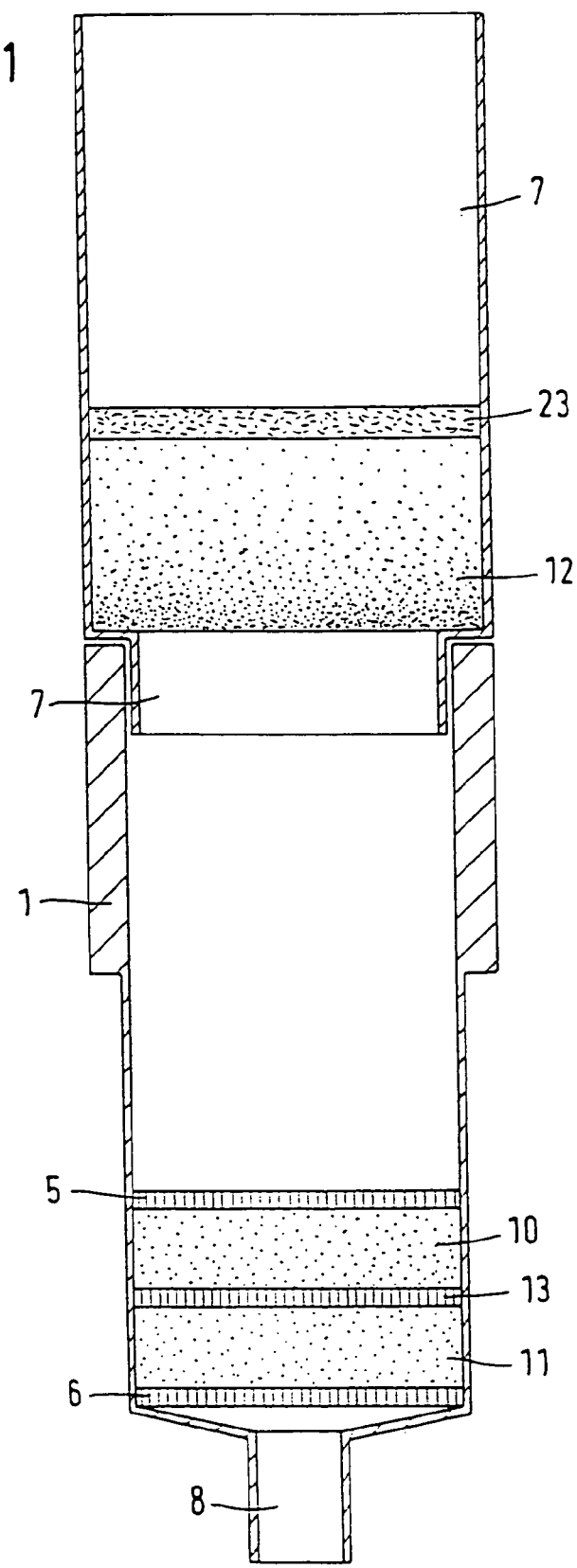

FIG. 11 describes a configuration in a combination of FIGS. 9 and 10. Here, the device described in FIG. 2 is merely provided with a filter head consisting of an asymmetric filter 12 and a hydrophobic filter layer 23, such as by inserting an appropriately designed cartridge.

All the individual devices described in more detail in FIGS. 1 to 5 and 7 to 11 may be arranged in a microtiter strip consisting of 8 lined-up single devices. Once more, this is exemplified in FIGS. 12 to 14.

Figure 12:
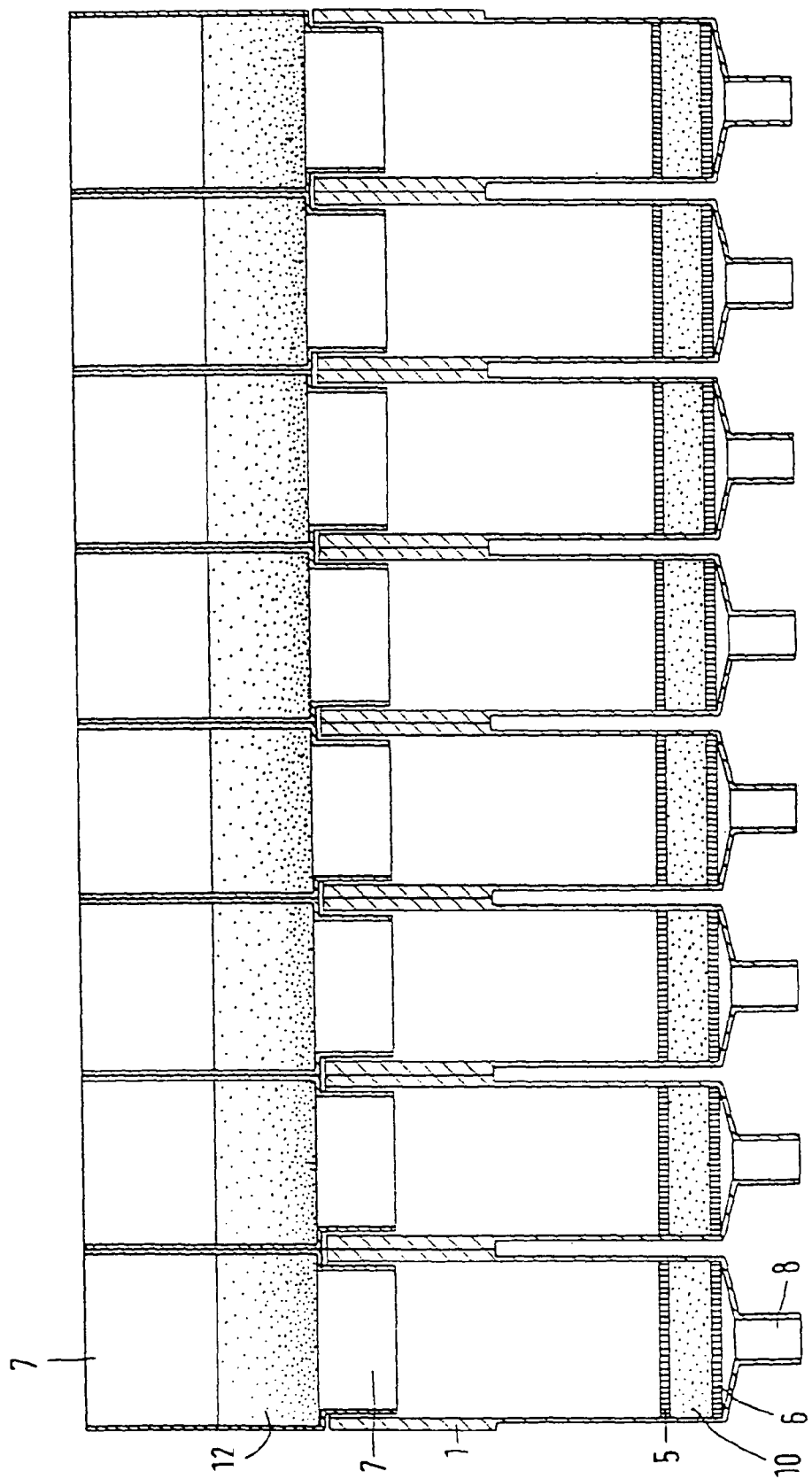

FIG. 12 illustrates a filtration device including an anion exchanger, a microtiter strip or a microtiter plate having 8 and/or 8×12 wells. In the device according to FIG. 12, there is placed an asymmetric filtration device in an attachable cartridge on top of the cylindrical hollow body 1 containing a layer of anion exchanger secured between means 5 and 6.

Figure 13:
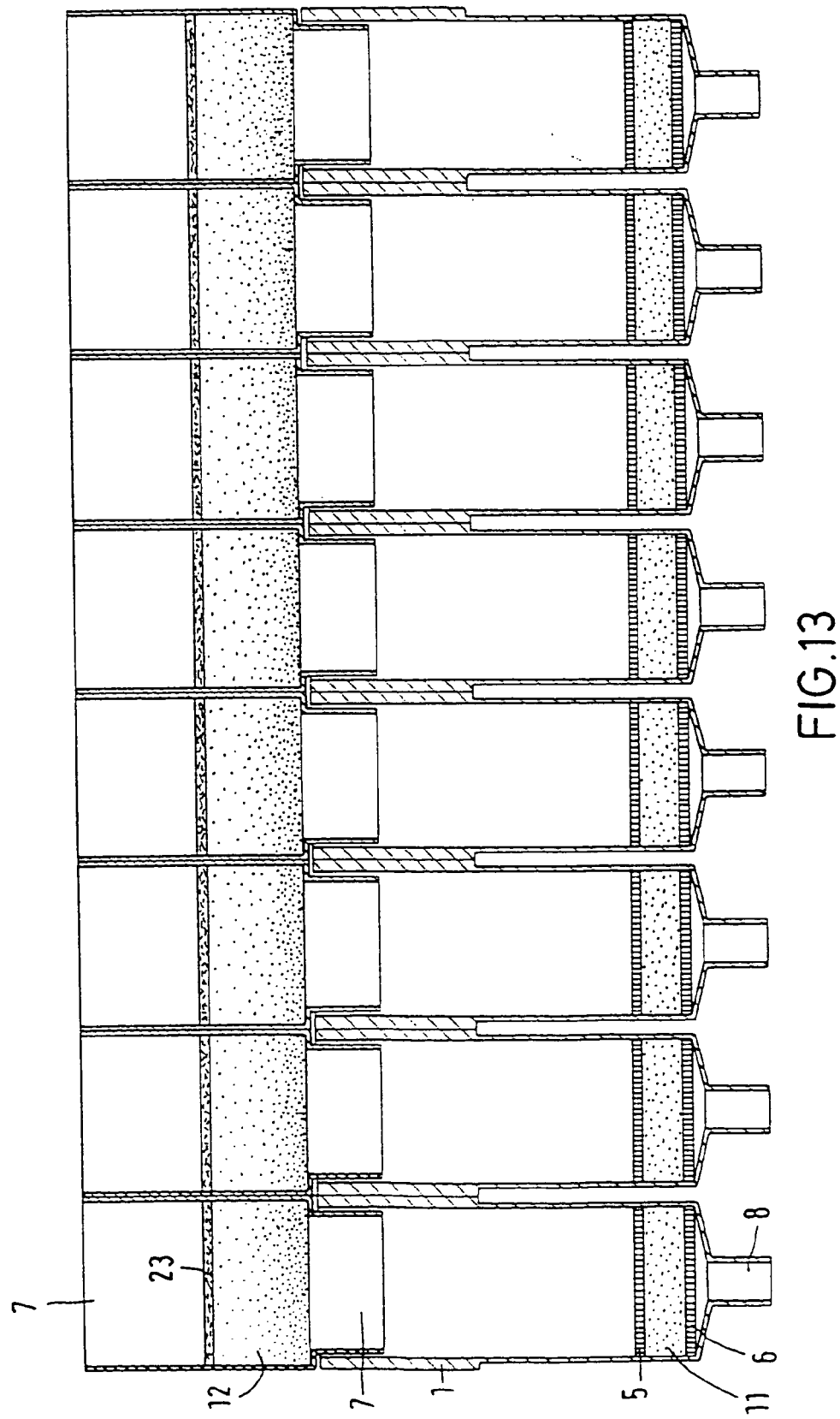

FIG. 13 relates to a filtration device having instead of the anion exchanger material a mineral support material capable of adsorbing nucleic acids in high salt concentrations. Preferably, a silica gel layer 11 is arranged between two means 5 and 6.

Figure 14:
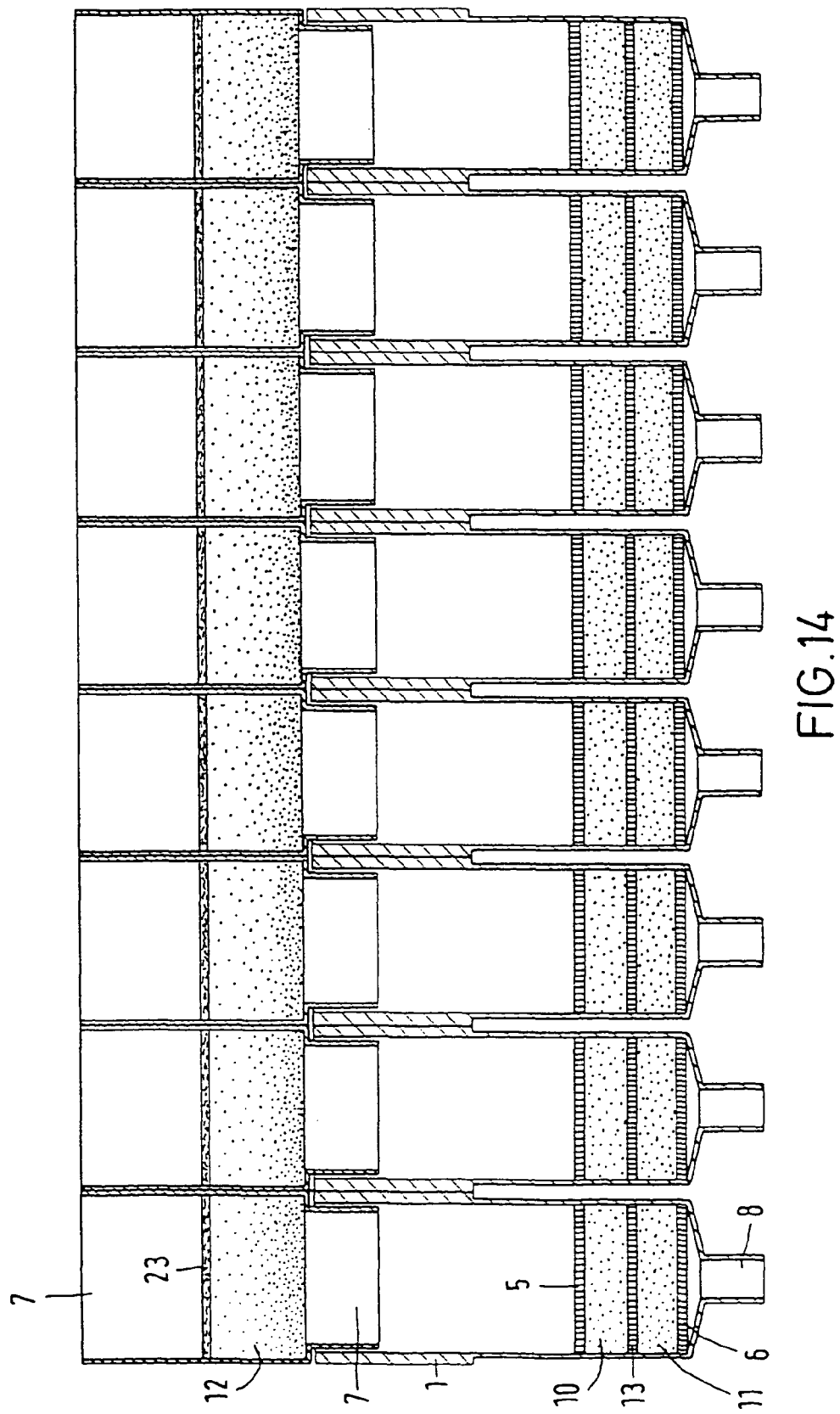

FIG. 14 illustrates a combination of the arrangement according to FIG. 2 and an asymmetric filter layer with a hydrophobic filter layer arranged above hollow body 1 as viewed in sample flow direction.

The device according to the invention, particularly the devices discussed in more detail in FIG. 3 or 4, are particularly advantageous in that elution of nucleic acid from the second material with use of very low amounts of liquid is ensured.

Basically, sample flow through the device according to the invention is induced by gravity; however, in order to enhance purification and separation of the nucleic acids, elevated pressure may be applied at opening 7 or reduced pressure at opening 8 or 18. A further preferred embodiment of the device according to the invention uses as the asymmetric filters those made of sintered glass having decreasing pore size or stacked plastic membranes having decreasing pore size in flow direction of the sample through the hollow body.

Nucleic acids from cells and other sources my be obtained without centrifugation, phenol/chloroform extraction and without alcohol precipitation, with the nucleic acid being present at the end of the process in concentrated form in water or buffer of low salt concentration and thus, is directly usable for subsequent enzymatic reactions. Another advantage is that use of costly laboratory equipment can be avoided. For example, elution may be induced by gravity and does not have to be carried out by means of so-called HPLC devices.

Preferably, preparation of a silica gel anion exchanger/ silica gel extraction column is accomplished in that a polypropylene vessel is sealed fittingly into a commercially available 1.5 ml centrifugation vessel having a 50 µm bottom polyethylene frit (porous filter layer of polyethylene, 1.5 mm thick) and is layered with 50 mg of silica gel (Lichrosphere Si 100, 16-24 µm; Merck, Darmstadt, Germany). This silica gel layer is sealed with a second porous polyethylene frit, and the second frit is layered with 100 mg of silica gel anion exchanger (Qiagen, Diagen Co.; Düsseldorf, Germany), particle size 16 to 23 µm, and finally, is sealed with a third porous polyethylene frit.

Preferably, preparation of an agarose anion exchanger/ silica gel extraction column is accomplished in that a polypropylene vessel is sealed at the bottom with a 50 µm polyethylene frit (porous filter layer of PE; 1.5 mm thick) and is layered with 50 mg of silica gel (Lichrosphere Si 100, 16-24 µm; Merck, Darmstadt, Germany). This silica gel layer is sealed with a second porous polyethylene frit, and the second frit is layered with 0.5 ml of DEAE Sepharose FF (Pharmacia Co., Freiburg, Germany), particle size 45 to 165 µm, and finally, is sealed with a third porous polyethylene frit.

Preferably, preparation of an anion exchanger membrane/ silica gel membrane extraction column according to FIG. 3 is accomplished in that into a polypropylene vessel on top of a polyethylene frit, there is placed a 1 mm thick Empore® silica gel membrane (3) (3M Corp., St. Paul, Minn., U.S.A.), a 0.2 mm thick polypropylene fleece and a 1 mm thick anion exchanger membrane consisting of 16-23 µm Qiagen anion exchanger particles (Diagen GmbH, Düsseldorf, Germany).

The preparation of an anion exchanger/silica gel microtiter strip extraction column is accomplished as described: A microtiter strip having 8 or 96 positions is charged with a DEAE silica gel membrane and a silica gel membrane. Into a boring of a microtiter strip, there are fitted a silica gel membrane 0.75 mm in thickness, prepared from Sident 9 silica gel particles (Degussa Co., Frankfurt, Germany), a polypropylene fleece layer 0.2 mm in thickness, and an anion exchanger membrane 0.8 mm in thickness, prepared from Qiagen, 16-23 µm (Diagen Co., Düsseldorf, Germany).

The invention will be further illustrated by the following Examples.

EXAMPLE 1

Preparation of Plasmid DNA

A 100 ml culture in LB ampicillin medium including pUC 18-transformed HB 101 *E. coli* cells is centrifuged at 5,000 g for 10 minutes. The cell pellet is resuspended in 10 ml of 50 mM Tris-HCl, 10 mM EDTA, pH 8.0, and 100 µg/ml of RNase A.

For cell lysis, 10 ml of 0.2 M NaOH and 1% SDS are added to the cell suspension, mixed carefully, and allowed to stand at room temperature for 5 minutes. This is followed by neutralization using 10 ml of 3 M potassium acetate, 2 M acetic acid, mixing and incubation on ice for 15 minutes. The lysate is centrifuged at 15,000 g for 30 minutes, and the supernatant is removed carefully. 1 ml of clear cell lysate is pipetted onto a DEAE anion exchanger/silica gel centrifugation extraction column, and the sample is centrifuged through the exchanger layer for 1 minute at 2,500 g. The extraction column is washed with 0.8 ml of 1 M NaCl, 15% ethanol, 50 mM MOPS, pH 7.0, and 15% ethanol, 10 mM sodium acetate, pH 7.0, and 0.8 ml of 1 M NaClO$_4$ to remove RNA and proteins. The DNA is eluted with 7 M NaClO$_4$, 15% ethanol, 10 mM sodium acetate, pH 7.0, and thereby, directly bonded to the silica gel layer. The extraction column is washed with 0.8 ml of 70% ethanol, 100 mM NaCl, 10 mM sodium acetate, pH 7.0, and 0.8 ml of 90% ethanol/water. Optionally, traces of ethanol are removed by further centrifugation. Subsequently, the DNA is eluted by centrifugation using 50 µl of 10 mM Tris-HCl, 1 mM EDTA, pH 8.0, and collected in new 1.5 ml tubes. The eluted DNA may then be used directly in enzymatic reactions such as, restriction, labeling, sequencing, or amplification.

EXAMPLE 2

Parallel Preparation of Plasmid DNA

8 DEAE silica gel membrane/silica gel extraction columns are attached onto a vacuum chamber. 8× of each 1 ml of a cell lysate containing plasmid DNA are passed through the extraction columns by suction under a vacuum (20 to 750 mbars.). The extraction column is washed with 0.8 ml of 1 M NaCl, 15% ethanol, 50 mM MOPS, pH 7.0, and 15% ethanol, 10 mM sodium acetate, pH 7.0, and 0.8 ml of 1 M NaClO$_4$ to remove RNA and proteins. The DNA is eluted from the anion exchanger layer with 7 M NaClO$_4$, 15% ethanol, 10 mM sodium acetate, pH 7.0, and thereby, directly bonded to the silica gel layer. The extraction column is washed with 0.8 ml of 70% ethanol, 100 mM NaCl, 10 mM sodium acetate, pH 7.0, and 0.8 ml of 90% ethanol/water. In order to remove the highly concentrated salt solution, the sample tubes are washed with 0.8 ml of 70% ethanol, 100 mM NaCl, 10 mM sodium acetate, pH 7.0, and 0.8 ml of 90% ethanol/water. The ethanol/H$_2$O residues present in the extraction layer are volatilized by sucking through ambient air by vacuum for 1-2 minutes. Subsequently, the 8 samples are eluted with 50 µl of 1 mM Tris-HCl, 0.1 mM EDTA, pH 8.0.

EXAMPLE 3

Preparation of M13 Single Stranded DNA

To 1 ml of M13 phage suspension are added 0.5 ml of 30% PEG 6000, 1.5 M NaCl, and following incubation on ice for 10 minutes, this is centrifuged off for 15 minutes at 15,000 g. The phage pellet is resuspended in 0.5 ml of 0.5 M guanidine-HCl, 1% Triton X-100 and lysed at 70° C. for 10 minutes. According to Example 3, the phage lysate is sucked through an extraction column on a vacuum chamber and adsorbed. The extraction column is washed with 1 ml of 0.75 M NaCl, 15% ethanol, 50 mM MOPS, pH 7.0, 1 ml of 0.75 M NaClO$_4$, 50 mM Tris-HCl, pH 7.0, eluted from the anion exchanger layer with 7 M guanidine, 15% ethanol, 50 mM sodium acetate, pH 7.0, and adsorbed to the SiO$_2$ layer.

EXAMPLE 4

Preparation of Genomic DNA from Blood

To 1 ml of citrate-stabilized human whole blood is added 1 ml of saponin for erythrocyte lysis, and immediately subsequent to mixing is centrifuged at 2,500 g for 5 minutes. The leukocytes are resuspended in 1 ml of PBS buffer and repelletized. The washed leukocytes are resuspended in 1 ml of 500 mM guanidine-HCl, 50 mM Tris-HCl, 10 mM EDTA, pH 8.0, and the cells are lysed by adding 0.1 ml of proteinase K (10 mg/ml) at 50° C. for 2 hours. The leukocyte lysate is pipetted immediately onto the agarose/anion exchanger/silica gel/extraction column and washed with 1 ml of 0.25 M NaCl, 10 mM sodium acetate, pH 7.0, and 1 ml of 0.25 M NaClO$_4$, 10 mM sodium acetate, pH 7.0. 1 ml of citrate-stabilized human whole blood is sucked through an anion exchanger/silica gel column under vacuum. Thereby, the leukocytes are trapped within the matrix, while the substantially smaller erythrocytes migrate through the matrix. The extraction column is re-washed twice using 1 ml of PBS buffer. The trapped leukocytes are lysed with 10% Tween 10 at room temperature for 15 minutes. Cell fragments and proteins are washed out twice using 1 ml of 1 M guanidine-HCl, pH 7.0, and the DNA is eluted from the column with 7 M NaClO$_4$, 50 mM sodium acetate, pH 7.0.

EXAMPLE 5

Preparation, Desalting and Concentration of DNA in Micro-Titer Format

96×1 ml cultures of plasmid pBluescript in XL 1 Blue *E. coli* cells are cultured in 2×YT medium for 18 hours at 37° C. in a microtiter plate having 1.5 ml wells (Beckmann Co., Munich). The cells are pelletized in a microtiter centrifuge at 2,500 g for 10 minutes. Using an 8 channel pipette (Matrix Technologies Co., Lowell, Mass., U.S.A.) each 0.25 ml of 50 mM Tris-HCl, 10 mM EDTA, 100 µg/ml RNAg1A are pipetted into the microtiter plate wells, and the cells are resuspended on a vibratory shaker for 5 minutes.

The cells are lysed by adding each 0.25 ml of 0.2 M NaOH, 1% SDS for 5 minutes at room temperature with slight shaking. Subsequently, each 0.25 ml of 3 M potassium acetate, 2 M acetic acid, pH 5.5-6.0 neutralization buffer is added, and each well is sealed with a cap and mixed. Following incubation on ice for 10 minutes, the sample is centrifuged at 3,000 g for 30 minutes to pelletize cell fragments and precipitated SDS. The supernatant is removed carefully using an 8 channel pipette and pipetted into the 96 microtiter plate having a DEAE silica gel membrane and a silica gel membrane. Subsequent to transferring all the 96 samples, the samples are sucked through the microtiter plate by applying a vacuum to the filtration apparatus. Thereby, the DNA is adsorbed to the anion exchanger layer, whereas proteins, RNA and metabolites are not adsorbed under such conditions.

The extraction column is washed with 0.8 ml of 1 M NaCl, 15% ethanol, 50 mM MOPS, pH 7.0, and with 15% ethanol, 10 mM sodium acetate, pH 7.0, and 0.8 ml of 1 M NaClO$_4$ to remove RNA and proteins. The DNA is eluted with 7 M NaClO$_4$, 15% ethanol, 10 mM sodium acetate, pH 7.0, and thereby, directly bonded to the silica gel layer. The extraction column is washed with 0.8 ml of 70% ethanol, 100 mM NaCl, 10 mM sodium acetate, pH 7.0, and 0.8 ml of 90% ethanol/water. Subsequently, the salt-free DNA in concentrated form is eluted from the silica gel layer into another microtiter plate using 50 µl of 1 mM Tris-HCl, 0.1 mM EDTA, pH 8.0.

The preparation of cell lysates with the aid of centrifugation is a lengthy and expensive process. Primarily, limitation is given in cases where many samples have to be prepared in routine. Centrifugation suffers from the drawback that it cannot be automatized.

Another subject matter (and process) of the invention is a device and a process for the automatic operation of the process without centrifugation in the form of a filtration unit upstream from the actual nucleic acid purification.

Here, the sample is lysed in known manner using proteinases, detergents and/or temperature or alkali. This crude lysate is directly decanted, transferred or pipetted onto the filtration head. The filter layer of the filtration head is designed in such way that jamming of the filters by cell debris, precipitated proteins or detergents is avoided. The cell lysate is pressed through the filter layer with a piston or by elevated pressure or is sucked through by applying a vacuum. Thereby, all the undissolved components are retained, and the clear lysate drips directly onto the adsorption layer. By selecting the appropriate adsorption conditions the nucleic acid is adsorbed to the adsorption layer. The filtration unit including the filter cake is detached from the adsorption unit and/or discarded and is saved for analysis of the filter cake. The adsorption unit is rewashed with suitable solvents or buffers to remove undesirable components, and eventually, the desired sample is eluted using a suitable elution agent.

According to the process of the invention, for example, plasmid DNA may be prepared without clarifying centrifugation in a refrigerated centrifuge. 96×1 ml cultures of plasmid pBluescript in XL1 Blue *E. coli* cells are cultured in 2×YT medium for 18 hours at 37° C. in a microtiter plate having 1.5 ml wells (Beckmann Co., Munich). The cells are pelletized in a microtiter centrifuge at 2,500 g for 10 minutes.

Using an 8 channel pipette (Matrix Technologies Co., Lowell, Mass., U.S.A.) each 0.25 ml of 50 mM Tris-HCl, 10 mM EDTA, 100 µg/ml RNAg1A are pipetted into the microtiter plate wells, and the cells are resuspended on a vibratory shaker for 5 minutes. The resuspended cells are transferred to the sample reservoir of the filtration head, and 0.25 ml of 0.2 M NaOH/1% SDS is added thereto. The sample is shaken for 5 minutes on a vibratory shaker or is sealed with a stopper or an adhesive film and mixed, or is mixed by repeated pipetting up and down.

Following 5 minutes of incubation at room temperature for lysis, 0.25 ml of 3 M potassium acetate and 2 M acetic acid are added and mixed according to one of the above-described procedures, in order to neutralize NaOH and precipitate SDS. Now, instead of centrifugation on a vacuum chamber, this crude cell lysate is sucked through the filtration layer at a vacuum of 10-800 mbars. A filter layer 2-10 mm in thickness and having an asymmetric or stepwise porosity in the range of from 200 to 5 µm retains the cell fragments and other undissolved or precipitated components without jamming. The clear cell lysate containing plasmid DNA drips through the filter layer onto the adsorption layer (anion exchanger or silica gel), and the DNA is adsorbed, whereas proteins, RNA and other cellular metabolites do not bind under the salt conditions given. Filtration is completed after about 10-60 s. The filter head is detached and is discarded together with the filter cake.

The bound DNA is washed with 1 ml of 1 M NaCl, 15% ethanol, 50 mM Tris-HCl, pH 7.0, and twice with 1.5 M NaClO$_4$, 10 mM sodium acetate, pH 6.5, and is eluted from the anion exchanger with 7 M NaClO$_4$, 15% ethanol, 50 mM Tris-HCl, pH 7.0, and after passing the separation layer, under the high salt concentrations is immediately bound to the silica gel layer from a Nylon net or a PP fleece. Here, at 1-2 M NaClO$_4$, proteins and RNA do not bind to the silica gel layer and are washed off. To remove remaining traces of proteins, the silica gel layer is washed with 1 ml of 7 M guanidine-HCl, 10 mM sodium acetate, pH 7.0. Conveniently, the high salt solution of 7 M NaClO$_4$ is washed off with 1 ml of 70% EtOH, 100 mM NaCl, 10 mM sodium acetate, pH 7.0, and 1 ml of 90% ethanol/water or 1 ml of 90% acetone/water. Subsequent to drying, the plasmid DNA is eluted free of salt and in concentrated form with 50 µl of 1 mM Tris-HCl, 0.1 mM EDTA, pH 8.5.

In this fashion, the plasmid DNA may be isolated in concentrated form in no time at all, without centrifugation, phenol/chloroform extraction and without alcoholic precipitation, with yields ranging from 50-80%. When using a microtiter plate type such as described, 96 plasmid minipreps of 1-2 ml of *E. coli* cultures may be prepared within 60 minutes by a single person, yielding from 1 to 10 µg of DNA. With hitherto known processes, from 6 to 12 hours are required.

EXAMPLE 6

Plasmid Miniprep Using a Device According to FIG. 7

A 1.5 ml XL Blue *E. coli* culture with pUC 18 plasmid DNA in LB medium is centrifuged at 10,000 g for 5 minutes to pelletize the cells. The cell pellet is resuspended in 0.25 ml of 50 mM Tris-HCl, 10 mM EDTA, pH 8.0, 100 µg/ml of RNase A. For cell lysis, 0.25 ml of 0.2 M NaOH and 1% SDS are added to the cell suspension, mixed carefully, and allowed to stand at room temperature for 5 minutes. This is followed by neutralization using 0.25 ml of 3 M potassium acetate, 2 M acetic acid, mixing and incubation on ice for 15 minutes. The lysate is transferred to the filtration device according to FIG. 7. The entire device is attached on top of a vacuum chamber, and the cell lysate is sucked through the device at 20-800 mbars. Alternatively, the sample may be pressed through the filtration layers using a piston or elevated pressure. Following filtration, the filtration device is detached, and the filter cake, together with cell fragments, denatured proteins and precipitated SDS, is discarded.

The extraction column is washed twice with 0.8 ml of 1 M NaCl, 15% ethanol, 50 mM MOPS, pH 7.0, to remove RNA and proteins. The DNA is eluted with 1 ml of 1.25 M NaCl, 15% ethanol, 50 mM Tris-HCl, pH 8.5. For desalting and concentrating, the eluted DNA is precipitated with alcohol, and the alcohol pellet is pelletized by centrifugation.

EXAMPLE 7

Preparation of Plasmid DNA Using a Device According to FIG. 8

A 1.5 ml XL Blue *E. coli* culture with pUC 18 plasmid DNA in LB medium is centrifuged at 10,000 g for 5 minutes to pelletize the cells. The cell pellet is resuspended in 0.25 ml of 50 mM Tris-HCl, 10 mM EDTA, pH 8.0, 100 mg/ml of RNase A and is transferred to the filtration device. For cell lysis, 0.25 ml of 0.2 M NaOH and 1% SDS are added to the cell suspension into the filtration device according to FIG. 8, the device is sealed with a stopper or an adhesive film, mixed carefully, and allowed to stand at room temperature for 5 minutes. This is followed by neutralization using 0.25 ml of 3 M potassium acetate, 2 M acetic acid, mixing and incubation on ice for 15 minutes. The entire device is attached on top of a vacuum chamber, and the cell lysate is sucked through the device at 20-800 mbars. Alternatively, the sample may be pressed through the filtration layers using a piston or elevated pressure. Following filtration, the filtration device is detached, and the filter cake, together with cell fragments, denatured proteins and precipitated SDS, is discarded. The extraction column is washed twice with 0.8 ml of 1 M NaCl, 15% ethanol, 50 mM MOPS, pH 7.0, to remove RNA and proteins. The DNA is eluted with 1 ml of 1.25 M NaCl, 15% ethanol, 50 mM Tris-HCl, pH 8.5. For desalting and concentrating, the eluted DNA is precipitated with alcohol, and the alcohol pellet is pelletized by centrifugation.

EXAMPLE 8

Preparation of Plasmid DNA at a Silica Gel Layer Using a Device According to FIG. 10

A 1.5 ml XL Blue *E. coli* culture with pUC 18 plasmid DNA in LB medium is centrifuged at 10,000 g for 5 minutes to pelletize the cells. The cell pellet is resuspended in 0.25 ml of 50 mM Tris-HCl, 10 mM EDTA, pH 8.0, 100 µg/ml of RNase A and is transferred to the filtration device. For cell lysis, 0.25 ml of 0.2 M NaOH and 1% SDS are added to the cell suspension into the filtration device, the device is sealed with a stopper or an adhesive film, mixed carefully, and allowed to stand at room temperature for 5 minutes. This is followed by neutralization using 0.5 ml of 5.5 M guanidine-HCl, 0.25 M potassium acetate, pH 5.5, mixing and incubation on ice for 15 minutes. The entire device according to FIG. 10 is attached on top of a vacuum chamber, and the cell lysate is sucked through the device at 20-800 mbars. Alternatively, the sample may be pressed through the filtration layer using a piston or elevated pressure. Following filtration, the filtration device is detached, and the filter cake, together with cell fragments, denatured proteins and precipitated SDS, is discarded. The extraction column is washed twice with 1 ml of 7 M NaClO$_4$, 10 mM sodium acetate, pH 7.0, and is washed with 0.8 ml of 90% ethanol/water, and traces of ethanol are sucked through. Eventually, the DNA is eluted with 50 µl of 10 mM Tris-HCl, 1 mM EDTA, pH 8.0, and is collected in new 1.5 ml tubes.

The eluted DNA may be used directly in enzymatic reactions such as, e.g., restriction, labeling, sequencing, or amplification.

EXAMPLE 9

Preparation of 8× Plasmid DNA in a Microtiter Strip

8×1.5 ml of XL Blue *E. coli* culture with pUC 18 plasmid DNA in LB medium is centrifuged at 10,000 g for 5 minutes to pelletize the cells. The cell pellets are resuspended in 0.25 ml of 50 mM Tris-HCl, 10 mM EDTA, pH 8.0, 100 µg/ml of RNase A and are transferred to the device according to FIG. 14. For cell lysis, 0.25 ml of 0.2 M NaOH and 1% SDS are added to the cell suspension into the filtration device, the device is sealed with a stopper or an adhesive film, mixed carefully, and allowed to stand at room temperature for 5 minutes. This is followed by addition of 0.25 ml of 3 M potassium acetate, 2 M acetic acid for neutralization, mixing and incubation on ice for 15 minutes. The entire device is attached on top of a vacuum chamber, and the cell lysate is sucked through the device at 20-800 mbars. Alternatively, the sample may be pressed through the filtration layers using elevated pressure. Following filtration, the filtration device is detached, and the filter cake, together with cell fragments, denatured proteins and precipitated SDS, is discarded. The extraction column is washed with 0.8 ml of 1 M NaCl, 15% ethanol, 50 mM MOPS, pH 7.0, and with 0.8 ml of 1 M NaClO$_4$, 15% ethanol, 10 mM sodium acetate, pH 7.0, to remove RNA and proteins. The DNA is eluted from the anion exchanger layer 10 using 7 M NaClO$_4$, 15% ethanol, 10 mM sodium acetate, pH 7.0, and thereby, directly bonded to the silica gel layer 11. The extraction column is washed with 0.8 ml of 70% ethanol, 100 mM NaCl, 10 mM sodium acetate, pH 7.0, and 0.8 ml of 90% ethanol/water. The ethanol/H$_2$O residues present in the extraction layer are volatilized by sucking through ambient air by vacuum for 1-2 minutes. Subsequently, the 8 samples are eluted with 50 µl of 1 mM Tris-HCl, 0.1 mM EDTA, pH 8.0.

EXAMPLE 10

Preparation of 8×1 ml of M13 DNA Using a Device According to FIG. 13

To 8×1 ml of M13 phage suspension, there is added 0.5 ml of 30% PEG 6000, 1.5 M NaCl, and this is incubated on ice for 10 minutes. The samples are transferred to a device according to FIG. 13, and the phage lysate is directly sucked through a device according to FIG. 13 on a vacuum chamber and filtrated. The phage pellet is lysed by sucking through 7 M guanidine-HCl, pH 7.0, and at the same time, the DNA is adsorbed to the silica gel layer 11. The extraction column is washed with 0.8 ml of 70% ethanol, 100 mM NaCl, 10 mM sodium acetate, pH 7.0, and with 0.8 ml of 70% ethanol, 100 mM NaCl, 100 mM sodium acetate, pH 7.0, and with 0.8 ml of 90% ethanol/water, and air is sucked through for 1-2 minutes. Eventually, the DNA is eluted with 50 µl of 10 mM Tris-HCl, 1 mM EDTA; pH 8.0, and is collected in new 1.5 ml tubes.

The eluted DNA may then be used directly in enzymatic reactions such as, e.g., restriction, labeling, sequencing, or amplification.

EXAMPLE 11

Preparation of 8×12 Plasmid DNA Using a Device According to FIG. 14

96×1.5 ml XL Blue E. coli cultures with pUC 18 plasmid DNA in LB medium are centrifuged at 2,500 g for 5 minutes to pelletize the cells. The cell pellets are resuspended in 0.25 ml of 50 mM Tris-HCl, 10 mM EDTA, pH 8.0, 100 µg/ml of RNase A and are transferred to the device and sealed with a stopper or an adhesive film, mixed carefully, and allowed to stand at room temperature for 5 minutes. This is followed by neutralization using 0.25 ml of 3 M potassium acetate, 2 M acetic acid, mixing and incubation on ice for 15 minutes. The entire device is attached on top of a vacuum chamber, and the cell lysate is sucked through the device at 20-800 mbars. Alternatively, the sample may be pressed through the filtration layers using elevated pressure. Following filtration, the filtration device is detached, and the filter cake, together with cell fragments, denatured proteins and precipitated SDS, is discarded. The extraction column is washed twice with 0.8 ml of 1 M NaCl, 15% ethanol, 50 mM MOPS, pH 7.0, and with 0.8 ml of 1 M NaClO$_4$, 15% ethanol, 10 mM sodium acetate, pH 7.0, to remove RNA and proteins. The DNA is eluted from the anion exchanger layer 10 with 7 M NaClO$_4$, 15% ethanol, 10 mM sodium acetate, pH 7.0, and thereby, directly bonded to the silica gel layer 11. The extraction column is washed with 0.8 ml of 70% ethanol, 100 mM NaCl, 10 mM sodium acetate, pH 7.0, and 0.8 ml of 90% ethanol/water.

The ethanol/H$_2$O residues present in the extraction layer are volatilized by sucking through ambient air by vacuum for 1-2 minutes. Subsequently, the 96 samples are eluted with each 50 µl of 1 mM Tris-HCl, 0.1 mM EDTA, pH 8.0, and collected in new 1.5 ml tubes. The eluted DNA may be used directly in an enzymatic reaction such as, e.g., restriction, labeling, sequencing, or amplification.

EXAMPLE 12

Preparation of Plasmid DNA without Conditioning

A 3 ml culture in LB ampicillin medium including pUC 18-transformed HB 101 E. coli cells is centrifuged at 5,000 g for 10 minutes. The cell pellet is resuspended in 0.25 ml of 50 mM Tris-HCl, 10 mM EDTA, pH 8.0, and 100 µg/ml of RNase A. For cell lysis, 0.25 ml of 0.2 M NaOH and 1% SDS are added to the cell suspension, mixed carefully, and allowed to stand at room temperature for 5 minutes. This is followed by neutralization using 0.25 ml of 3 M potassium acetate, 2 M acetic acid, mixing and incubation on ice for 15 minutes. The lysate is centrifuged at 10,000 g for 15 minutes, and the supernatant is removed carefully. The clear cell lysate is pipetted onto a DEAE anion exchanger/extraction column, and the sample is sucked through the exchanger layer. The extraction column is washed with 0.8 ml of 1 M NaCl, 15% ethanol, 50 mM MOPS, pH 7.0, and 15% ethanol, 10 mM sodium acetate, pH 7.0, to remove RNA and proteins. The DNA is sucked onto an extraction column having a glass fiber membrane, using 7 M NaClO$_4$, 15% ethanol, 10 mM sodium acetate, pH 7.0. The eluted DNA solution in 7 M NaClO$_4$ is sucked through the glass fiber membrane, and thereby, directly bonded to the silica gel layer. The extraction column is washed with 0.8 ml of 70% ethanol, 100 mM NaCl, 10 mM sodium acetate, pH 7.0, and with 0.8 ml of 90% ethanol/water. Optionally, traces of ethanol are removed by sucking through ambient air. Finally, the DNA is eluted with 10 µl of 10 mM Tris-HCl, 1 mM EDTA, pH 8.0, and collected in new 1.5 ml tubes.

EXAMPLE 13

Preparation of Plasmid DNA with Conditioning

A 3 ml culture in LB ampicillin medium including pUC 18-transformed HB 101 E. coli cells is centrifuged at 5,000 g for 10 minutes. The cell pellet is resuspended in 0.25 ml of 50 mM Tris-HCl, 10 mM EDTA, pH 8.0, and 100 µg/ml of RNase A. For cell lysis, 0.25 ml of 1.2 M NaOH and 1% SDS are added to the cell suspension, mixed carefully, and allowed to stand at room temperature for 5 minutes. This is followed by neutralization using 0.25 ml of 3 M potassium acetate, 2 M acetic acid, mixing and incubation on ice for 15 minutes. The lysate is centrifuged at 10,000 g for 15 minutes, and the supernatant is removed carefully. The clear cell lysate is pipetted onto a DEAE anion exchanger/extraction column, and the sample is sucked through the exchanger layer. The extraction column is washed with 0.8 ml of 1 M NaCl, 15% ethanol, 50 mM MOPS, pH 7.0, to remove RNA and proteins, and conditioning is effected using 0.8 ml of 1 M NaClO$_4$, 15% ethanol, 10 mM sodium acetate, pH 5.0. The DNA is sucked onto an extraction column having a glass fiber membrane, using 0.7 ml of 7 M NaClO$_4$, 15% ethanol, 10 mM sodium acetate, pH 7.0. This glass fiber membrane has been conditioned in advance using 0.2 ml of 7 M NaClO$_4$, 15% ethanol, 10 mM sodium acetate, pH 7.0, to achieve better DNA adsorption and to avoid losses in the first drops. Subsequently, the eluted DNA solution in 7 M NaClO$_4$ is sucked through the glass fiber membrane on a vacuum device and thereby, is directly bonded to the silica gel layer. The extraction column is washed with 0.8 ml of 70% ethanol, 100 mM NaCl, 10 mM sodium acetate, pH 7.0, and with 0.8 ml of 90% ethanol/water. Optionally, traces of ethanol are removed by sucking through ambient air. Finally, the DNA is eluted with 100 µl of 10 mM Tris-HCl, 1 mM EDTA, pH 8.0, and collected in new 1.5 ml tubes.

Preconditioning may also be achieved using a membrane which has been soaked with 7 M NaClO$_4$, 15% ethanol, 10 mM sodium acetate, pH 7.0, and dried. This preconditioning reduces adsorption losses from 30% to below 5%, and the overall yield of DNA increases from 50-60% to 80-90%.

The invention claimed is:

1. A process for the isolation and purification of nucleic acids from cells comprising, in two separation/purification stages, the steps of:
  i) in a first separation/purification stage,
    a) digesting the cells containing nucleic acids, removing cell debris and thereafter subjecting the nucleic acids to anion exchange against an anion exchanger in a first buffer solution, which has a low ionic strength, b) desorbing the nucleic acids from the anion exchanger by applying a second buffer solution, which has a higher ionic strength than the first buffer solution, effecting purified nucleic acids in the second buffer solution; and ii) in a second separation/purification stage, c) adsorbing the separation/purified nucleic acids in the second buffer solution onto the surface of a mineral support material, optionally in the presence of lower alcohols, poly(ethylene glycol), or a mixture thereof, and d) desorbing the nucleic acids from the mineral support material by applying an eluant, wherein the eluant is water or a third buffer solution, which has an ionic strength lower than the second buffer solution, effecting twice-purified nucleic acids.

2. The process according to claim 1, wherein the stages i) and ii) are carried out in immediate succession.

3. The process according to claim 1, further comprising the step of, prior to the digesting step, subjecting the cells to centrifugation or filtration in order to remove undissolved components.

4. The process according to claim 1 further comprising, between the steps a) and b), one or more washing steps by applying a fourth buffer solution, which has a low ionic strength, optionally increasing ionic strength per washing step.

5. The process according to claim 1 further comprising, between the steps c) and d), one or more washing steps by applying a fifth buffer solution, which has an ionic strength higher than the first buffer solution.

6. The process according to claim 1 further comprising, between the steps c) and d), at least one washing step by applying an aqueous alcoholic solution.

7. The process of claim 6, wherein the aqueous alcoholic solution includes from 1 to 7 M sodium perchlorate, from 1 to 7 M guanidine-HCl, from 1 to 5 M sodium chloride, from 1 to 6 M sodium iodide, or 1 M sodium chloride in a 20% alcoholic solution wherein the alcoholic portion of the alcoholic solution is selected from the group consisting of ethanol, propanol, isopropanol, butanol, poly(ethylene glycol), and mixtures thereof.

8. The process according to claim 1 further comprising, between the steps c) and d), a washing step by applying a solution having an ionic strength corresponding to a 1.5 molar sodium perchlorate solution and a pH of 5.

9. The process according to claim 1, wherein the isolated and purified nucleic acid has from 10 nucleotides to 200,000 nucleotides.

10. The process according to claim 1, wherein the mineral support material is silica gel, glass, zeolite, aluminum oxide, titanium dioxide, zirconium dioxide, kaolin, or diatomacae.

11. The process according to claim 1, wherein the anion exchanger has a porous or non-porous matrix having a particle size of from 1 to 250 μm.

12. The process according to claim 1, wherein the anion exchanger has a porous or non-porous matrix having a particle size of from 10 to 30 μm.

13. The process according to claim 1, wherein the mineral support is silica gel, in suspension, having a particle size of from 1 to 250 μm.

14. The process according to claim 1, wherein the mineral support is silica gel, in suspension, having a particle size of from 1 to 5 μm.

15. The process according to claim 1, wherein the anion exchanger has a particle size of from 1 to 250 μm and a pore diameter of from 1 to 2,500 nm.

16. The process according to claim 1, wherein the anion exchanger has a particle size of from 10 to 100 μm and a pore diameter of from 1 to 2,500 nm.

17. The process according to claim 1, wherein the anion exchanger has a particle size of from 1 to 250 μm and a pore diameter of from 100 to 400 nm.

18. The process of claim 1, wherein the eluant is a buffer solution that comprises water and Tris at a pH value of from 5 to 9.

19. The process of claim 1, whereby the nucleic acids are plasmid or genomic DNA.

* * * * *